United States Patent [19]

Rath et al.

[11] Patent Number: 5,112,364
[45] Date of Patent: May 12, 1992

[54] GASOLINE-ENGINE FUELS CONTAINING POLYETHERAMINES OR POLYETHERAMINE DERIVATIVES

[75] Inventors: Hans P. Rath, Gruenstadt; Helmut Mach, Heidelberg; Knut Oppenlaender, Ludwigshafen; Willibald Schoenleben, Heidelberg; Hans-Henning Vogel, Frankenthal, all of Fed. Rep. of Germany

[73] Assignee: BASF Aktiengesellschaft, Ludwigshafen, Fed. Rep. of Germany

[21] Appl. No.: 697,529

[22] Filed: Apr. 29, 1991

Related U.S. Application Data

[63] Continuation of Ser. No. 379,935, Jul. 14, 1989, abandoned.

[30] Foreign Application Priority Data

Aug. 5, 1988 [DE] Fed. Rep. of Germany ....... 3826608

[51] Int. Cl.$^5$ ............................ C10L 1/18; C10L 1/22
[52] U.S. Cl. ............................ 44/418; 44/422; 44/424; 44/434
[58] Field of Search ............. 44/434, 418, 422, 424, 44/72, 71, 73; 252/71

[56] References Cited

U.S. PATENT DOCUMENTS

| | | | |
|---|---|---|---|
| 463,256 | 7/1985 | Valone | 564/348 |
| 2,229,024 | 1/1941 | Bruson | 260/268 |
| 3,440,029 | 4/1969 | Little et al. | 44/75 |
| 4,100,078 | 7/1978 | Kleber et al. | 252/8.9 |
| 4,144,035 | 3/1979 | Moss et al. | 44/71 |
| 4,261,704 | 4/1981 | Langdon | 44/62 |
| 4,304,690 | 12/1981 | Schulze et al. | 252/526 |
| 4,332,595 | 6/1982 | Herbstman et al. | 44/72 |
| 4,429,160 | 1/1984 | Linquenheld et al. | 564/505 |
| 4,564,372 | 1/1986 | Campbell | 44/71 |
| 4,568,358 | 2/1986 | Courtney | 44/57 |
| 4,604,103 | 8/1986 | Campbell | 44/72 |
| 4,609,377 | 9/1986 | Sung et al. | 44/56 |
| 4,964,879 | 10/1990 | Herbstman et al. | 44/434 |

FOREIGN PATENT DOCUMENTS

| | | | |
|---|---|---|---|
| 221108 | 1/1958 | Australia | 564/347 |
| 242487 | 9/1959 | Australia | 564/347 |
| 0100665 | 2/1984 | European Pat. Off. | |
| 0289785 | 11/1988 | European Pat. Off. | |
| 821204 | 12/1957 | France | 564/347 |
| 2334656 | 7/1977 | France | |
| 191406 | 8/1937 | Switzerland | |
| 498328 | 7/1937 | United Kingdom | 564/347 |
| WO8501956 | 5/1985 | World Int. Prop. O. | |

OTHER PUBLICATIONS

Ege, Organic Chemistry, D. C. Heath and Co. p. 158.
PCT WO 85/01956 "Deposit Control Additives-Hydroxy Polyether Polyamines", Campbell, 9/5/85.

*Primary Examiner*—Jacqueline Howard
*Attorney, Agent, or Firm*—Keil & Weinkauf

[57] ABSTRACT

Gasolines containing polyetheramine and/or polyetheramine derivatives to improve valve cleaning properties.

8 Claims, No Drawings

GASOLINE-ENGINE FUELS CONTAINING POLYETHERAMINES OR POLYETHERAMINE DERIVATIVES

This application is a continuation of application Ser. No. 07/379,935, filed on Jul. 14, 1989, now abandoned.

The present invention relates to gasoline-engine fuels which contain small amounts of a polyetheramine and/or a polyetheramine derivative, wherein the polyetheramine is prepared by reductive amination of a phenol-initiated or alkylphenol-initiated polyether and the polyetheramine derivative is prepared by reacting the polyetheramine with an alkylene oxide or a carboxylic acid.

Polyetheramines are known fuel additives for cleaning carburetors, injectors and valves and for keeping them clean and form the subject of, for example, PCT Application WO 85/01956 or EP-B 1 0 100 665.

These publications describe compounds which are prepared starting from ethylenechlorohydrin, by oxyalkylation, etherification of the terminal hydroxyl group and substitution of the chlorine atom by an amino group.

Although these polyetheramines are excellent valve cleaners having a pronounced cleaning effect in the intake system of the engine, they have the disadvantage of having a residual chlorine content from the preparation. However, fuel additives or oil additives which contain chlorine are undesirable for reasons of corrosion and of environmental protection.

It is an object of the present invention to provide chlorine-free polyetheramines which are suitable fuel additives. It is a further object of the present invention to improve the action of the known polyetheramines or to achieve the same effect using a smaller dose.

We have found that this object is achieved and that, surprisingly, gasoline-engine fuels which contain small amounts of polyetheramines and/or polyetheramine derivatives have a very good valve-cleaning and carburetor-cleaning action, and contain no chlorine, if the polyetheramines and polyetheramine derivatives are those the general formula

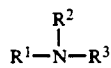
(I)

or

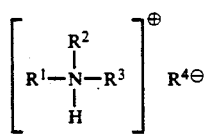
(II)

where $R^1$ is a phenolpolyether or alkylphenolpolyether radical of the general formula

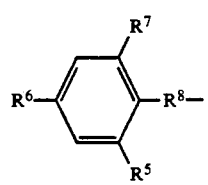
(IIIa)

or a cyclohexylpolyether or alkylcyclohexlpolyether radical of the general formula

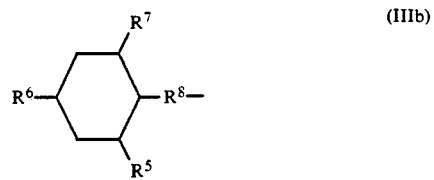
(IIIb)

$R^2$ and $R^3$ may be identical or different and are each hydrogen, a phenolpolyether or alkylphenolpolyether radical (IIIa), a cyclohexylpolyether or alkylcyclohexylpolyether radical (IIIb), an acyl radical of a carboxylic acid of 2 to 24 carbon atoms or a hydroxyalkyl radical of the general formula

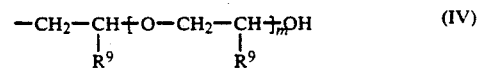
(IV)

or $R^2$ is alkyl of 1 to 20 carbon atoms and $R^3$ is hydrogen, a phenolpolyether or alkylphenolpolyether radical (IIIa), a cyclohexylpolyether or alkylcyclohexylpolyether radical (IIIb), an acyl radical of a carboxylic acid of 2 to 24 carbon atoms or a hydroxyalkyl radical (IV), $R^4$ is a carboxylate radical of a carboxylic acid of 2 to 24 carbon atoms, $R^5$, $R^6$ and $R^7$ may be identical or different and are each hydrogen or a hydrocarbon radical of 1 to 30 carbon atoms, $R^8$ is a polyether chain obtained from an alkylene oxide of 2 to 8 carbon atoms or a mixture of such alkylene oxides, having from 2 to 100 alkylene oxide units in the chain, and $R^9$ is hydrogen or a hydrocarbon radical of 1 to 6 carbon atoms and m is from 0 to 5, the mean molecular weight $M_n$ of the polyetheramines or polyetheramine derivatives (I) or (II), respectively, being from 00 to 8,000 and the polyetheramines, or the polyetheramines on which the polyetheramine derivatives are based, being prepared by reductive amination of phenolpolyethers or alkylphenolpolyethers of the general formula

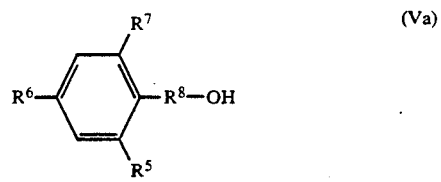
(Va)

or of cyclohexylpolyethers or alkylcyclohexylpolyethers of the general formula

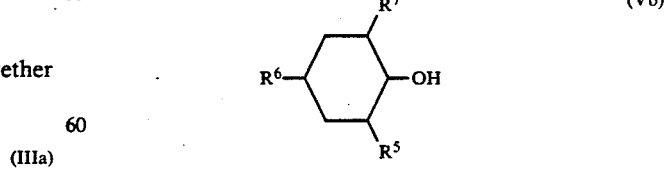
(Vb)

where $R^5$, $R^6$, $R^7$ and $R^8$ have the stated meanings, with ammonia or a primary amine.

The polyetheramines and polyetheramine derivatives to be used according to the invention are generally synthesized in several stages. In a first step, a phenolpolyether or alkylphenolpolyether of the general formula (Va) or a cyclohexylpolyether or alkylcyclohexylpolyether of the general formula (Vb) is prepared in a conventional manner, advantageously by oxyalkylating phenol or an alkylphenol of the general formula

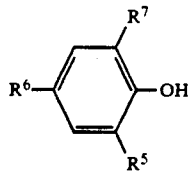
(VIa)

or cyclohexanol or an alkylcyclohexanol of the general formula

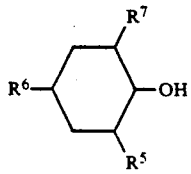
(VIb)

where $R^5$, $R^6$ and $R^7$ have the abovementioned meanings, with an alkene oxide of 2 to 8 carbon atoms or a mixture of such alkylene oxides. The oxyalkylation is carried out in the presence or absence of an alkali, such as potassium hydroxide solution, sodium hydroxide solution or sodium methylate, advantageously at elevated temperatures, for example at from 80° to 140° C., preferably from 100° to 120° C.

Suitable radicals $R^5$, $R^6$ and $R^7$ are hydrogen and straight-chain or preferably branched, hydrocarbon radicals of 1 to 30 carbon atoms, particularly preferred hydrocarbon radicals being methyl and branched hydrocarbon radicals of 3 to 16 carbon atoms. Suitable initiators in addition to phenol and the cresols are, in particular, alkylated phenols and cresols.

Examples are isobutylphenol, isobutylcresol, diisobutylphenol, diisobutylcresol, tert-butylphenol, tert-butylcresol, di-tert-butylphenol, di-tert-butylcresol, isooctylphenol, diisooctylphenol, isononylphenol, diisononylphenol, isododecylphenol, diisododecylphenol and mixtures of these.

The alkylphenols to be used as initiators are obtained in a conventional manner, for example by alkylation of phenols, cresols or dimethylphenols with the corresponding olefins. The alkylcyclohexanols likewise to be used as initiators are obtained, for example, by hydrogenation of the nucleus of corresponding alkylphenols.

The oxyalkylation of phenol or of the alkylphenols or of the cyclohexanol or of the alkylcyclohexanols with the alkylene oxides of 2 to 8, preferably 3 to 6, carbon atoms, in particular propylene oxide and/or butylene oxide, such as 1,2-butylene oxide, 2,3-butylene oxide or isobutylene oxide, is carried out in a conventional manner, the reaction with the butylene oxides being preferred. A general method of preparation is described below. For example, the reaction is carried out using only one alkylene oxide, for example with propylene oxide or butylene oxide, or with a mixture of alkylene oxides, for example a mixture of propylene oxide and butylene oxide. The reactions with the alkylene oxide, for example propylene oxide or butylene oxide, or with a mixture of alkylene oxides, for example a mixture of propylene oxide and butylene oxide, may be carried out in one stage. However, it may also be advantageous if the compounds obtained in the first stage are reacted with further alkylene oxide, such as propylene oxide or butylene oxide or a mixture of alkylene oxides, for example a mixture of propylene oxide and butylene oxide, in a second stage or in more than two stages, two stages being preferred. The amount of alkylene oxide, for example propylene oxide or butylene oxide, can vary within fairly wide limits. As a rule, from 3 to 100, preferably from 5 to 30, moles of alkylene oxide are used per mole of initiator. The amount used and the choice of the alkylene oxide, in general propylene oxide or butylene oxide, depends, however, on which initiator molecule has been used. If the initiator molecule contains a long-chain hydrophobic radical, such as diisododecylphenol, larger amounts of low molecular weight alkylene oxides, preferably propylene oxide, can be used. If, on the other hand, the initiator molecule contains shorter-chain hydrophobic radicals, it may be advantageous to use alkylene oxides having a higher molecular weight, preferably butylene oxide, or, for example in mixtures of propylene oxide and butylene oxide, to increase the proportion of butylene oxide.

In general, the alkylene oxides and their amount are chosen so that a minimum solubility of 50% by weight in a hydrocarbon, for example toluene or mineral oil SN 100, is ensured for the production of a masterbatch.

In a second stage, the polyethers are then subjected to amination by a conventional method, in general without further pretreatment. Amination is the reaction of the polyethers (Va) and (Vb) with ammonia or a primary amine, the terminal OH group in the polyether being replaced by an amino group with elimination of water. The method is described in detail in Houben-Weyl 11/1, Chapter IIb, pages 108–134, which is hereby incorporated by reference.

As in all reductive aminations, the remaining free hydrogen atoms on the nitrogen of the amino group can be replaced by further polyether radicals (III), so that, as a rule, a mixture of amines is formed, for example in the amination with ammonia a mixture of primary, secondary and tertiary amines, for example in a weight ratio of 6:3:1. In the amination with a primary amine, a mixture of secondary and tertiary amines is accordingly formed.

The amination reaction is advantageously carried out at from 160° to 250° C. and under pressures of up to 600, preferably 80–300, bar. Preferred catalysts are cobalt-containing and nickel-containing catalysts on carriers such as $SiO_2$ or $Al_2O_3$, but also Raney nickel or Raney cobalt itself. Quantitative conversion of the OH groups is not necessary for the intended use, especially when the polyethers used as starting compounds of the formulae (Va) and (Vb) are also used as carrier oil for the gasoline additive formulation. Partial conversion may even be advantageous since higher space-time yields are obtained. In general, the ammonia or the amine is used in excess, for example in a 10-fold to 60-fold, preferably 15-fold to 40-fold, molar excess, in the amination. Ammonia is preferably used. Primary amines used for the amination are those having an alkyl radical of 1 to 20, preferably 1 to 13, in particular 1 to 8, carbon atoms. Examples are methylamine, ethylamine and butylamine.

The polyetheramines obtained by amination can be added as such to the fuels.

However, they can also be converted into the corresponding derivatives in a conventional manner by reaction with alkylene oxides or carboxylic acids, and added in the form of the derivatives to the fuels.

In the derivatization of the polyetheramines with alkylene oxides, those of 2 to 8, preferably 2 to 4, carbon atoms are used, for example propylene oxide, butylene oxide and in particular ethylene oxide. The alkoxylation with the alkene oxides is carried out in a conventional manner, advantageously in the presence of an alkali, such as potassium hydroxide solution, sodium hydroxide solution or sodium methylate, at elevated temperatures, for example at from 120° to 150° C. A general method of preparation is described below.

In the resulting derivatives having the hydroxyalkyl radicals of the general formula (IV), m is from 0 to 5, derivatives having one chain member (m=0) being preferred.

The derivatization of the polyetheramines by reaction with carboxylic acids can be carried out on the one hand by neutralization with the formation of the corresponding ammonium salts, the polyetheramine derivatives of the formula (II) being obtained. The neutralization is carried out in a conventional manner. The general method of preparation is described below.

The derivatization of the polyetheramines with carboxylic acids can also be carried out by amidation with formation of the carboxamides, i.e. to give polyetheramine derivatives of the formula (I), where $R^2$ and/or $R^3$ are acyl radicals. The amidation is carried out in a conventional manner. A general method of preparation is described below.

In general, monocarboxylic acids of 2 to 24, preferably 2 to 10, carbon atoms are used as carboxylic acids for the neutralization or amidation. Examples of suitable carboxylic acids are acetic acid, propionic acid, valeric acid, caproic acid, caprylic acid, pelargonic acid, capric acid, lauric acid, palmitic acid, stearic acid, oleic acid, isononanoic acid and 2-ethylhexanoic acid.

Suitable fuels are leaded and unleaded regular and premium grade gasoline. The gasolines may also contain components other than hydrocarbons, for example alcohols, such as methanol, ethanol, tert-butanol, and ethers, e.g. methyl tert-butyl ether. In addition to the polyetheramines or polyetheramine derivatives to be used according to the invention, the fuels contain, as a rule, further additives, such as corrosion inhibitors, stabilizers, antioxidants, detergents, etc.

Corrosion inhibitors are generally ammonium salts of organic carboxylic acids, which tend to form films as a result of the starting compounds having appropriate structure. Amines, for increasing the pH, are also frequently present in corrosion inhibitors. Heterocyclic aromatics are generally used for corrosion protection of nonferrous metals.

Particular examples of antioxidants or stabilizers are amines, such as para-phenylenediamine, dicyclohexylamine, morpholine and derivatives of these amines. Phenolic antioxidants, such as 2,4-di-tert-butylphenol or 3,5-di-tert-butyl-4-hydroxyphenylpropionic acid and its derivatives, are also added to fuels and lubricants.

Amides and imides of polyisobutylenesuccinic anhydride, polybuteneamines, polybutenepolyamines and long-chain carboxamides and -imides may also be present in the fuels, as carburetor, injector and valve detergents.

Mineral oils of the viscosity range SN 500–900 as well as brightstock and synthetic oils, such as polyalpha-olefins, trimellitic esters or polyethers, in particular those based on alkylphenol and butene oxide, can be used as carrier oils for masterbatches of the polyetheramines to be used according to the invention, or their derivatives.

The esters should contain very long-chain, branched alcohols of more than 8 carbon atoms, and the polyethers should preferably contain long-chain initiators and have high propylene oxide or butylene oxide contents, based on the amount of alkylene oxide, in the molecule.

The fuels contain the polyetheramines or polyetheramine derivatives of the formula (I) or (II) as a rule in amounts of from 10 to 2,000 ppm by weight, based on the pure polyetheramine or polyetheramine derivative. In general, however, as little as from 20 to 1,000, preferably from 40 to 400, ppm by weight are sufficient.

The preparation of the polyetheramines and polyetheramine derivatives and their effect in the engine are described in detail below.

PREPARATION EXAMPLE

1. Reaction of phenol or alkylphenol with alkylene oxides

The polyethers are prepared by known methods of oxyalkylation with an alkali.

In an autoclave having a stirrer, 0.1% by weight, based on the total batch, of finely powdered KOH is dispersed in the alkylphenol with stirring, and the mixture is heated to 130° C. under 200 mbar. Residual traces of water are removed during this procedure. The autoclave is then sealed and alkylene oxide is metered in so that a pressure of 6 bar is not exceeded. Different alkylene oxides may be metered in simultaneously or in succession, so that random polyethers or block polyethers having more or less well defined transitions are formed. After the alkylene oxides have been fed in, the pressure decreases to 2–3 bar in the course of from 3 to 10 hours. Once this pressure has been reached, the autoclave is cooled to 80° C., the pressure is let down via a membrane valve and the autoclave is evacuated down to 20–30 mbar. After the reduced pressure has been maintained for about 1 hour, an equivalent amount of an acidic ion exchanger is then added to remove potassium and the mixture is filtered.

2. Reductive amination of the polyethers

The polyethers prepared according to Preparation Example 1 are generally subjected to the subsequent amination with ammonia or a primary amine without further pretreatment. However, where the polyether has a fairly high viscosity, it is advisable to dilute it with a solvent, preferably a branched aliphatic, such as isododecane, so that a viscosity of 50–200 mm$^2$/s at 20° C. is obtained. For example, the polyethers, as such or in solution with ammonia, which is generally used in excess, for example in a 2-fold to 100-fold, preferably 10-fold to 80-fold, molar excess, is treated with hydrogen, for example for from 10 minutes to 10 hours, in the presence of a hydrogenation catalyst, e.g. Raney nickel, under superatmospheric pressure, for example from 10 to 300, preferably from 50 to 250, bar, in a pressure reactor, for example a rotating autoclave, at elevated temperatures, for example from 80° to 300° C., preferably from 120° to 250° C. After the mixture has been cooled, the catalyst is separated off by filtration, excess ammonia is evaporated and the water of reaction is distilled off azeotropically or under a gentle stream of nitrogen.

3. Derivatization of polyetheramines

The polyetheramines prepared according to Examples 1 and 2 can be derivatized by known methods with alkene oxides or carboxylic acids. For this purpose, the amine number of the polyetheramine is advantageously first determined, for example using 0.1 M HCl against bromophenol blue.

a) Oxyalkylation

The reaction with epoxides is carried out in general as described under 1, in the presence of an alkaline catalyst, such as KOH, NaOH, NaOCH$_3$, etc., which is used in an amount of from 0.1 to 3% by weight, based on the polyetheramine. The reaction temperatures are from 120° to 150° C., depending on the epoxide, the reaction times are from 3 to 6 hours and the pressures are from 3 to 6 bar. The reaction is carried out in a stirred pressure container, the epoxides being added a little at a time. If more than from 1 to 2 moles of alkylene oxide are to be added, the process is advantageously carried out as a multistage process, preferably as a two-stage process as described below. The primary or secondary ether amine is first racted with from 1 to 2 moles of epoxide at from 100° to 120° C. in the presence of a small amount of water (3 to 5% by weight, based on the etheramine). In the case of secondary amines, the corresponding N-hydroxyalkyl compound is predominantly obtained, and in the case of primary amines the corresponding bis-OH-alkylamino derivative. Water is then removed under reduced pressure (for example from 15 to 30 mbar) at, for example, from 80° to 100° C., a small amount of an alkaline catalyst is added and the procedure described under 1 or 3 a is caried out for reaction with the remaining amount of epoxide. The products are characterized by the amine number and hydroxyl number and by the increase in weight.

b) Neutralization

The reaction components are advantageously reacted in stoichiometric amounts with stirring and gentle heating. However, it may be advantageous initially to take the etheramine and to add the carboxylic acid a little at a time.

c) Amidation

The reaction is carried out at elevated temperatures, advantageously at from 100° to 180° C., for example at from 150° to 160° C., with stirring of the reaction components used in stoichiometric amounts, in the presence or absence of a solvent, in an inert gas atmosphere (N$_2$), the amine advantageously being intially taken and the acid component added a little at a time. When the reaction is carried out in the absence of a solvent, the water of reaction is removed during the reaction under reduced pressure, for example under from 10 to 100 mbar, or by azeotropic distillation using a suitable entraining agent, for example an aromatic or aliphatic hydrocarbon, such as toluene, xylene, heavy gasoline, etc., in order to achieve as complete conversion as possible.

The reaction time is in general from 4 to 6 hours. The end of the reaction is detected by determining the acid number (less than 3), the amine number (less than 4) and the amount of water of reaction.

EXAMPLES

The following products were prepared by the methods stated above under 1, 2 and 3:

A: Isononylphenol is reacted with 1-butene oxide in a molar ratio of 1:19 according to Preparation Example 1. The resulting polyether has a viscosity of 220 mm$^2$/s at 40° C. and a theoretical molecular weight of 1,488. Amination is then carried out according to Preparation Example 2 at 100° C. and under 200 bar using a 50-fold molar excess of ammonia, over a nickel-coated catalyst in the presence of H$_2$, and a polyethyeramine is obtained in a yield of 94% with a residence time of 20 min. The viscosity of the product is 190 mm$^2$/s at 40° C., the molecular weight is 1,487 and the amine number is 30.4 (theoretical amine number 37.6).

B. Isononylphenol is reacted with 1-butene oxide in a molar ratio of 1:8 according to Preparation Example 1. The resulting polyether has a viscosity of 130 mm$^2$/s at 40° C. and a theoretical molecular weight of 796. It is reductively aminated as described under A. A polyetheramine having a viscosity of 100 mm$^2$/s at 40° C. and an amine number of 68 is obtained in a yield of 96%.

C: 2,6-Di-tert-butyl-p-cresol is reacted with propene oxide in a molar ratio of 1:9 according to Preparation Example 1. The resulting polyether has a viscosity of 80 mm$^2$/s at 40° C. and a molecular weight of 742. It is reductively aminated as described under A, the yield being 93%. The viscosity of the product is 60 mm$^2$/s at 40° C., the molecular weight is 741 and the amine number is 70.

D: Dinonylphenol is reacted with propene oxide in a molar ratio of 1:8 according to Preparation Example 1. The resulting polyether has a viscosity of 95 mm$^2$/s at 40° C. and a molecular weight of 810. The polyether thus obtained is reductively aminated with ammonia according to Preparation Example 2, as described under A. A polyetheramine having a viscosity of 80 mm$^2$/s at 40° C. and an amine number of 66 is obtained in a yield of 96%.

E: 100 parts of the compound prepared according to Example A are reached, by method 3a), with 2.75 parts of ethylene oxide, i.e. in a molar ratio of 1:1.

F: 100 parts of the compound prepared according to Example A are reacted, by method 3a), with 4.1 parts of ethylene oxide, i.e. in a molar ratio of 1:1.5.

G: 10 parts of isononanoic acid are added to 100 parts of the compound prepared according to Example A, an ammonium salt of the primary amine groups, which are predominantly present, being formed by method 3b), i.e. the molar ratio of amine to isononanoic acid is 1:1.

H: 10 parts of isononanoic acid are added to 100 parts of the compound prepared according to Example A, the compound being converted into the amine by method 3b). The molar ratio of amine to isononanoic acid is 1:1.

Procedure for the engine tests

The engine tests with the additives or additive packages were carried out on a Daimler Benz M 102 E engine using the cycling program stated below.

| Cycling program | | |
|---|---|---|
| Running time (s) | Speed (1/min) | Load (Nm) |
| 30 | 800 | 0 |
| 60 | 3000 | 8.34 |
| 60 | 1300 | 4.6 |
| 120 | 1850 | 5.44 |

The running time was 60 seconds and the number of cycles was 800. The fuel used was unleaded, alcohol-containing premium grade gasoline (3% of methanol, 2% of tert-butanol), and the engine oil used was the reference oil of the Opel Kadett test CEC-F-02-T-79, RL 51.

The intake valves are evaluated gravimetrically. For this purpose, the intake valves are removed and their lower surface is then carefully freed mechanically from deposits from the combustion space. Thereafter, superficially adhering, readily soluble constituents on the valves are removed by immersion in cyclohexane, and the valves are then dried by swinging them in the air. This treatment is repeated twice altogether. The intake valves are then weighed. The difference between the weight of the valve before the test and that after the test gives the amount of deposits per intake valve. The results of these tests are shown in Table 1.

TABLE 1

Testing of the intake valve contamination using a Daimler Benz M 102 E engine on the test stand with 300 mg of additive/kg of unleaded, alcohol-containing premium grade gasoline according to DIN 51,607, 280 1, engine oil RL 51, test duration 60 h

| No. | Additive from Example | Valve deposit in mg/intake valve |
|---|---|---|
| 1 | Base value | 343 |
| 2 | A | 16 |
| 3 | B | 22 |
| 4 | C | 18 |
| 5 | D | 34 |
| 6 | E | 9 |
| 7 | F | 18 |
| 8 | G | 21 |
| 9 | H | 30 |

We claim:

1. A gasoline-engine fuel containing per kg of fuel, 10 to 2000 mg of a polyetheramine and/or a polyetheramine derivative of

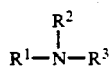

or

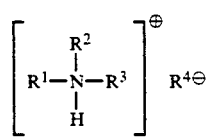

where $R^1$ is a phenolpolyether or alkylphenolpolyether radical of the formula

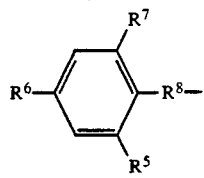

or a cyclohexylpolyether or alkylcyclohexylpolyether radical of the formula

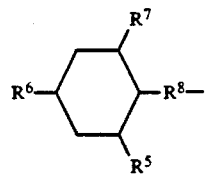

$R^2$ and $R^3$ may be identical or different and are each hydrogen, a phenolpolyether or alkylphenolpolyether radical (IIIa), a cyclohexylpolyether or alkylcyclohexylpolyether radical (IIIb), an acyl radical of a carboxylic acid of 2 to 24 carbon atoms or a hydroxyalkyl radical of the formula

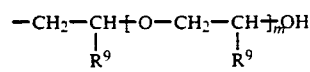

or $R^2$ is alkyl of 1 to 20 carbon atoms and $R^3$ is hydrogen, a phenolpolyether or alkylphenolpolyether radical (IIIa), a cyclohexylpolyether or alkylcyclohexylpolyether radical (IIIb), an acyl radical of a carboxylic acid of 2 to 24 carbon atoms or a hydroxyalkyl radical (IV), $R^4$ is a carboxylate radical of a carboxylic acid of 2 to 24 carbon atoms, $R^5$, $R^6$, and $R^7$ may be identical or different and are each hydrogen or a hydrocarbon radical of 1 to 30 carbon atoms, $R^8$ is a polyether chain obtained from butylene oxide, having from 2 to 100 butylene oxide units in the chain, and $R^9$ is hydrogen or a hydrocarbon radical of 1 to 6 carbon atoms and m is from 0 to 5, the mean molecular weight $M_n$ of the polyetheramines or polyetheramine derivatives (I) or (II), respectively, being from 500 to 8,000 and the polyetheramines, or the polyetheramines on which the polyetheramine derivatives are based, being prepared by reductive amination of phenolpolyethers or alkylphenolpolyethers of the formula

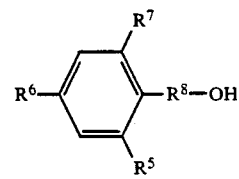

or of cyclohexylpolyethers or alkylcyclohexylpolyethers of the formula

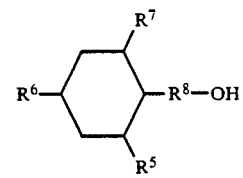

where $R^5$, $R^6$, $R^7$, and $R^8$ have the stated meanings, with ammonia or primary alkylmonamines with 1 to 20 carbon atoms at temperatures of from 160° to 250° C. and pressures up to 600 bars in the presence of nickel or cobalt containing catalysts.

2. A fuel as defined in claim 1, containing a polyetheramine of the formula (I), where $R^2$ and $R^3$ are each hydrogen.

3. A fuel as defined in claim 1, containing a polyetheramine of the formula (I), where $R^2$ is hydrogen and $R^3$ is acyl or a radical (IV) derived from ethylene oxide and in which m is 0 and $R^9$ is H.

4. A fuel as defined in claim 1, containing a polyetheramine derivative of the formula (II), where $R^4$ is the carboxylate radical of isononanoic acid or of ethylhexanoic acid.

5. A fuel as defined in claim 1, containing a polyetheramine and/or a polyetheramine derivative in which, in the phenolpolyether or alkylphenolpolyether radical of the formula (III), some or all of the radicals $R^5$, $R^6$ and $R^7$ are methyl and/or tert-butyl radicals.

6. A fuel as defined in claim 1, containing a polyetheramine and/or a polyetheramine derivative in which, in the phenolpolyether or alkylphenolpolyether radical of the formula (III), $R^5$ and $R^7$ are each tert-butyl and $R^6$ is methyl.

7. A fuel as claimed in claim 1, containing a polyetheramine and/or a polyetheramine derivative which are derived from alkylphenolpolyethers of the formula (V), which are prepared by oxyalkylation of the associated alkylphenols with butylene oxide.

8. A fuel as defined in claim 7, wherein the alkylphenolpolyethers are prepared by oxyalkylation of the associated alkylphenols with butylene oxide.

* * * * *

UNITED STATES PATENT AND TRADEMARK OFFICE
CERTIFICATE OF CORRECTION

PATENT NO. : 5,112,364

DATED : May 12, 1992

INVENTOR(S) : RATH et al.

It is certified that error appears in the above-identified patent and that said Letters Patent is hereby corrected as shown below:

Claim 7, Col. 11, Line 4

"claimed" should read --defined--

Signed and Sealed this

Thirteenth Day of July, 1993

Attest:

MICHAEL K. KIRK

Attesting Officer

Acting Commissioner of Patents and Trademarks